(12) United States Patent
Mattoussi et al.

(10) Patent No.: US 8,378,075 B2
(45) Date of Patent: Feb. 19, 2013

(54) COVALENT ATTACHMENT OF PEPTIDES AND BIOLOGICAL MOLECULES TO LUMINESCENT SEMICONDUCTOR NANOCRYSTALS

(75) Inventors: Hedi M Mattoussi, Tallahassee, FL (US); Philip E Dawson, San Diego, CA (US); Harry Tetsuo Uyeda, College Park, MD (US); Igor L Medintz, Springfield, VA (US); Johanna Scheinost, Oxford (GB)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 515 days.

(21) Appl. No.: 12/606,766

(22) Filed: Oct. 27, 2009

(65) Prior Publication Data

US 2011/0098445 A1    Apr. 28, 2011

(51) Int. Cl.
*C07K 14/00*    (2006.01)
(52) U.S. Cl. .............................. 530/350; 424/489; 514/2
(58) Field of Classification Search ........................ None
See application file for complete search history.

(56) References Cited

U.S. PATENT DOCUMENTS

| 6,326,144 | B1 | 12/2001 | Bawendi et al. | |
|---|---|---|---|---|
| 6,649,138 | B2 * | 11/2003 | Adams et al. ................. | 423/403 |
| 6,821,337 | B2 | 11/2004 | Bawendi et al. | |
| 6,855,551 | B2 | 2/2005 | Bawendi et al. | |
| 2002/0015679 | A1 | 2/2002 | Kotov | |
| 2006/0068506 | A1 | 3/2006 | Uyeda et al. | |
| 2007/0054337 | A1 | 3/2007 | Ferning et al. | |
| 2007/0249064 | A1 | 10/2007 | De La Fuente et al. | |
| 2008/0064121 | A1 | 3/2008 | Weiss et al. | |

FOREIGN PATENT DOCUMENTS

| WO | 0171043 | A1 | 9/2001 |
|---|---|---|---|
| WO | 03087824 | A2 | 10/2003 |
| WO | 2006060664 | A2 | 6/2006 |
| WO | 2007/013877 | A2 | 2/2007 |

OTHER PUBLICATIONS

Mattoussi, H., et al., "Self-assembly of CdSe-ZnS quantum dot bioconjugates using an engineered recombinant protein," J. Am. Chem. Soc., 122, 12142-12140 (2000).
Goldman, E.R., et al., "Conjugation of luminescent quantum dots with antibodies using an engineered adaptor protein to provide new reagents for fluoroimmunoassays," Anal. Chem., 74, 841-847 (2002).
Medintz, I.L., et al., "Nanoscale Biosensor Assemblies Built on Quantum Dot FRET Donors," Nature Materials, 2, 630-638 (2003).
Uyeda, H.T., et al., "Design of water-soluble quantum dots with novel surface ligands for biological applications," Mater. Res. Soc. Symp. Proc., 789. 111-116 (2004).
Chan, W.C.W., et al.. "Quantum Dot Bioconjugates for Ultrasensitive Nonisotopic Detection," Science 281, 2016-2018 (1998).
Medintz et al., "Quantum dot bioconjugates for imaging, labelling and sensing," Nat. Mater. Jun. 2005: 4(6); pp. 435-436.
Bruchez at el., Science 281, 2013 (1998).
Dabbousi et al., J. Phys. Chem. B, 101, 9463-9475 (1997).
Hines et al., J. Phys. Chem. 100, 468-471 (1996).
Miyawaki et al., Nature Cell Biology 5, S1-S7 (2003).
Murray et al., J. Am. Chem. Soc. 115, 8706-8713 (1993).
Sutherland, Curr. Op. Sol. St. Mat. Sci. 6, 365-370 (2002).
Uyeda et al., J. Am. Chem. Soc. 127, 3870-3878 (2005).
International Search Report and Opinion in PCT/US2010/054099.

* cited by examiner

*Primary Examiner* — Anand Desai
(74) *Attorney, Agent, or Firm* — Amy Ressing; Roy Roberts

(57) ABSTRACT

A method for covalent attachment of peptides to luminescent quantum dots or other inorganic nanoparticles. The first step in the method involves functionalizing at least a portion of a surface of the quantum dot or nanoparticle with one or more materials having at least one reactive functional group therein. Subsequently, a peptide having a reactive functional group is reacted with at least some of the quantum dot or nanoparticle reactive functional groups to covalently bond at least some of the peptide to the quantum dots or nanoparticles. Modifications of the basic method are disclosed which provide methods allowing customized fabrication of quantum dots having a variety of different functional properties and combinations of functional properties. Also disclosed are quantum dots and nanoparticles made by the methods of the present invention.

16 Claims, 11 Drawing Sheets

Peptides can be assembled from multiple smaller subunits

I — Protected amino acid: Fmoc-NH-CHR-COOH

II — Protected peptide fragment: Fmoc-GlyPheTyr(tBu)Lys(Boc)-OH

III — Side chain unprotected peptide fragment: x-Ser-Lys-His-Glu-y

X and Y are groups that react chemoselectively

| Functions Imparted by Peptides | Examples | Possible QD Uses |
|---|---|---|
| -Water Solubility/Passivation | Hydrophilic Peptides/glutathiones Phytochelatins | Water soluble biocompatible QDs |
| -Biofunctionality | AviTag/Biotin Protease Substrate | Fluorescent sensor Fluorescent label |
| -Biotargeting | Receptor Targeting/Hormones TAT peptide | Specific cellular receptor label |
| -Bioelectroconductivity | Peptides containing modified electroactive amino acids | Bio-electrochromic switches/sensors |
| -Contribute functional groups | Thiol, amine, carboxyl, hydroxy | Fluorescent nanoscaffold to monitor chemical rxns |

Figure 3

Scheme for creating a peptide surface consisting of peptides of different sequences and in different ratios by performing differential synthesis

```
SEQUENCE LISTING

<160> NUMBER OF SEQ ID NOS: 2

<210> SEQ ID NO 1
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: BINDING
<222> LOCATION: (1)..(1)
<223> OTHER INFORMATION: fluorenylmethyloxycarbonyl

<400> SEQUENCE: 1

Lys Gly Gly Arg Arg Arg Arg Arg Arg Arg
1               5                   10

<210> SEQ ID NO 2
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: BINDING
<222> LOCATION: (1)..(1)
<223> OTHER INFORMATION: fluorenylmethyloxycarbonyl

<400> SEQUENCE: 2

Lys Gly Gly Arg Arg Arg
1               5
```

COVALENT ATTACHMENT OF PEPTIDES AND BIOLOGICAL MOLECULES TO LUMINESCENT SEMICONDUCTOR NANOCRYSTALS

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A COMPACT DISK APPENDIX

Not applicable.

BACKGROUND OF THE INVENTION

The covalent chemical attachment of an active moiety to a carrier is a fundamental process that lies at the heart of a diverse range of scientific disciplines. For example, the attachment of peptides, oligosaccharides, DNA or small bioactive organic molecules to glass slides or chips has given rise to the enormous field of diagnostic screening, with example applications such as toxicological testing of new chemical entities and genetic products. Attachment of the same type of molecules to polymeric surfaces has applications in diverse fields such as affinity purification of small molecules/proteins and smart wound dressings that elicit a physiological response to enhance the wound healing process. Alternatively, attachment of such molecules to immunostimulatory proteins has application in the field of synthetic vaccine development. Within each of these fields, successful application is dependent upon the stringent control of a number of key chemical and physiochemical parameters being achieved.

A key objective is to obtain quantitative and qualitative control of the covalent attachment chemistry since this should provide a final construct that exhibits an optimal combination of molecular display and physiochemical characteristics. Each application has many subtle variations of these key requirements to consider, given the range of chemical diversity and intrinsic characteristics present in active moieties such as peptides, oligosaccharides, DNA or small bioactive organic molecules and the different physiochemical properties of a glass slide when compared to a polymeric bead or a protein.

International patent application publication no. WO 01/71043 discloses bonding of peptides and biological molecules to semiconductor nanocrystals using chemical coupling methods. Polynucleotides along with polypeptides and other polymeric biologicals are bound to semiconductor nanocrystals and dicarboxylic acids may be used as surface ligand linker molecules. This method appears to employ a functional group in the linker molecule (e.g. the dicarboxylic acid) for reaction with the peptide to achieve bonding. The semiconductor nanocrystals are typically bonded to a substrate or microsphere.

WO 03/087824, discloses coupling reactions using H-benzotriazol-1-yloxytris (dimethylamino) phosphonium hexafluorophosphate (BOP) in Example 1B. WO 06/060664, discloses coupling reactions using N-ethoxycarbonyl-2-ethoxy-1,2-dihydroquinoline (EEDQ) in Examples 1-2.

U.S. Pat. No. 6,326,144 discloses a reaction for coupling proteins and peptides to water soluble quantum dots. Specifically, Example 3 in column 19 couples avidin (a protein) to water soluble quantum dots using (1-[3-(dimethylamino)propyl]-3-ethylcarbodiimide hydrochloride) (EDAC) and N-hydroxysuccinimide (NHS).

U.S. patent application publication no. US 2006/0068506 A1 discloses a method for bonding a DNA biomolecule to a quantum dot in FIG. 9 and paragraph [0021]. In this method, dihydrolipoic or dihydrolipoic acid/polyethylene glycol-modified core shell quantum dots are bound to a DNA biomolecule using N-(3-dimethylaminopropyl)-N-ethylcarbodiimide (EDC) and N-hydroxysulfosuccinimide (sulfo-NHS) as coupling agents.

Methods for preparing water-soluble quantum dots involve the capping of core-shell nanocrystals with ionized dihydrolipoic acid molecules and more recently the use of poly(ethylene glycol) terminated dihydrolipoic acid (DHLA-PEG) ligands with PEGs of various sizes. Electrostatic self-assembly and the metal ion affinity of histidine coordinate techniques may be used to prepare bioconjugates. Electrostatic self-assembly takes advantage of positively charged domains of proteins coupled to negatively charged carboxylate groups on the quantum dot surface (Mattoussi, H., et al., "Self-assembly of CdSe—ZnS quantum dot bioconjugates using an engineered recombinant protein," *J. Am. Chem. Soc.*, 122, 12142-12140 (2000); Goldman, E. R., et al., "Conjugation of luminescent quantum dots with antibodies using an engineered adaptor protein to provide new reagents for fluoroimmunoassays," *Anal. Chem.*, 74, 841-847 (2002); and Medintz, I. L., et al., "Self-assembled nanoscale biosensors based on quantum dot FRET donors," *Nature Materials*, 2, 630-638 (2003)). Limitations of using electrostatic self-assembly combined with DHLA-capping are that activities must be carried out in a basic environment (pH>7) and there is an inability to form direct covalently linked nanocrystal-biomolecule conjugates in aqueous environments with N-3-(dimethylamino)-propyl-N'-ethyl-carbodiimide (EDC). Employing DHLA-PEG ligands permitted expansion of the range of pH solubility while still permitting electrostatic self-assembly (Uyeda, H. T., et al., "Design of water-soluble quantum dots with novel surface ligands for biological applications," *Mater. Res. Soc. Symp. Proc.*, 789, 111-116 (2004) and H. T. Uyeda et al., "Design of water-soluble quantum dots with novel surface ligands for biological applications," *J. Am. Chem. Soc.* 127, 3870-3878 (2005)).

Small organic surface ligands such as mercaptoacetic acid (MAA), aminoethane thiol (AET) and polymer encapsulation have been used to generate water-soluble quantum dot systems (Chan, W. C. W., et al., "Quantum Dot Bioconjugates for Ultrasensitive Nonisotopic Detection," *Science* 281, 2016-2018 (1998)). Water solubilization of quantum dots with hydrophilic dendritic structures and layer-by-layer assembly techniques have also been demonstrated with some degree of success. Such strategies, however, do not provide for pH stability and in some cases do not provide long-term water solubility. The major disadvantage of these systems is the poor temporal stability of the quantum dot-ligands due to the dynamic nature of the singly bound thiol groups, which results in aggregated solutions after a short time. Another disadvantage is the lack of the provision of compact hydrophilic quantum dots and quantum dot bioconjugates that can be easily delivered inside live cells and regions of cells and assay studies such as those based on fluorescence or Foster resonance energy transfer (FRET).

There remains a need in the art for improved coupling methods for covalent attachment of peptides and biological molecules to, for example, luminescent semiconductor nanocrystals or other nanoparticles.

BRIEF SUMMARY OF THE INVENTION

In a first aspect, the invention relates to a method for covalent attachment of peptides to quantum dots or nanoparticles. The first step in the method involves functionalizing at least a portion of a surface of the quantum dot or nanoparticle with one or more materials having at least one reactive functional group therein. Subsequently, a peptide having a reactive functional group is reacted with at least some of the quantum dot or nanoparticle reactive functional groups to covalently bond at least some of the peptide to the quantum dots or nanoparticles.

In other aspects, the present invention relates to modifications of the basic method above to provide methods allowing customized fabrication of quantum dots having a variety of different functional properties and combinations of functional properties.

In another aspect, the present invention relates to quantum dots and nanoparticles made by the methods of the present invention.

BRIEF DESCRIPTION OF THE DRAWINGS

FIG. 3 is an outline of some of the functions that may be imparted by peptides and/or the amino acids that are contained in the peptides and examples of some of the uses of quantum dots with such peptides synthesized on the surface thereof;

DETAILED DESCRIPTION OF THE INVENTION

Figure 1:
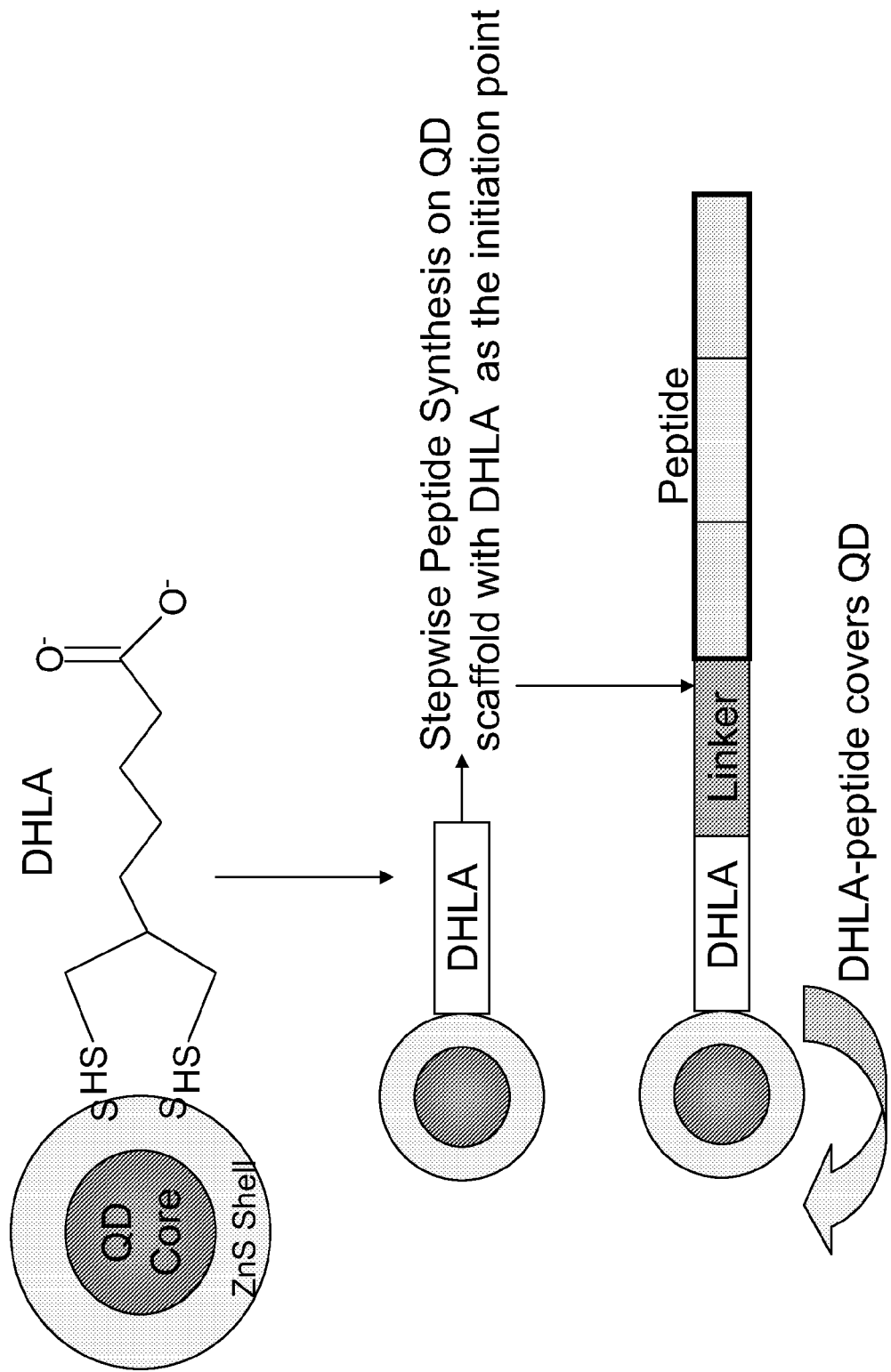
FIG. 1 is a generalized reaction scheme for synthesizing a peptide directly onto a dihydrolipoic acid (DHLA) covered quantum dot surface. Only one reaction is shown for simplicity but in practice the entire quantum dot is covered with DHLA and thus the peptide synthesis would extend out in all directions.

Before the present invention is described in detail, it is to be understood that this invention is not limited to the particular methodology, devices, solutions or apparatuses described, as such methods, devices, solutions or apparatuses can, of course, vary. It is also to be understood that the terminology used herein is for the purpose of describing particular embodiments only, and is not intended to limit the scope of the present invention.

Use of the singular forms "a," "an" and "the" include plural references unless the context clearly dictates otherwise. Thus, for example, reference to "a substrate" includes a plurality of such substrates.

Terms such as "connected," attached," "linked," and "conjugated" are used interchangeably herein and encompass direct as well as indirect connection, attachment, linkage or conjugation unless the context clearly dictates otherwise.

Where a range of values is recited, it is to be understood that each intervening integer value, and each fraction thereof, between the recited upper and lower limits of that range is also specifically disclosed, along with each sub-range between such values. The upper and lower limits of any range can independently be included in or excluded from the range, and each range where either, neither or both limits are included is also encompassed within the invention. Where a value being discussed has inherent limits, for example where a component can be present at a concentration of from 0 to 100%, or where the pH of an aqueous solution can range from 1 to 14, those inherent limits are specifically disclosed. Where a value is explicitly recited, it is to be understood that values which are about the same quantity or amount as the recited value are also within the scope of the invention. Where a combination is disclosed, each subcombination of the elements of that combination is also specifically disclosed and is within the scope of the invention. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

Unless defined otherwise or the context clearly dictates otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

All publications mentioned herein are hereby incorporated by reference for the purpose of disclosing and describing the particular materials and methodologies for which the reference was cited.

The term "antibody' as used herein includes antibodies obtained from both polyclonal and monoclonal preparations, as well as: hybrid (chimeric) antibody molecules (see, for example, Winter et al. (1991) Nature 349:293-299; and U.S. Pat. No. 4,816,567); F(ab')2 and F(ab) fragments; Fv molecules (noncovalent heterodimers, see, for example, Inbar et al. (1972) Proc. Natl. Acad. Sci. USA 69:2659-2662; and Ehrlich et al. (1980) Biochem 19:409 1-4096); single-chain Fv molecules (sFv) (see, for example, Huston et al. (1988) Proc. Natl. Acad. Sci. USA 85:5879-5883); dimeric and trimeric antibody fragment constructs; minibodies (see, e.g., Pack et al. (1992) Biocheyn 31:1579-1584; Cumber et al. (1992) J. Immunology 149B:120-126); humanized antibody molecules (see, for example, Riechmann et al. (1988) Nature 332:323-327; Verhoeyan et al. (1988) Science 239:1534-1536; and U. K. Patent Publication No. GB 2,276, 169, published 21 Sep. 1994); and, any functional fragments obtained from such molecules, wherein such fragments retain specific-binding properties of the parent antibody molecule.

As used herein, the term "monoclonal antibody" refers to an antibody composition having a homogeneous antibody population. The term is not limited regarding the species or source of the antibody, nor is it intended to be limited by the manner in which it is made. Thus, the term encompasses antibodies obtained from murine hybridomas, as well as human monoclonal antibodies obtained using human hybridomas or from murine hybridomas made from mice expression human immunoglobulin chain genes or portions thereof. See, e.g., Cote, et al. Monoclonal Antibodies and Cancer Therapy, Alan R. Liss, 1985, p. 77.

Polypeptide" and "protein" are used interchangeably herein and include a molecular chain of amino acids linked through peptide bonds. The terms do not refer to a specific length of the product. Thus, "peptides," "oligopeptides" and "proteins" are included within the definition of polypeptide. The terms include polypeptides containing post-translational modifications of the polypeptide, for example, glycosylations, acetylations, phosphorylations, and sulphations. In addition, protein fragments, analogs (including amino acids not encoded by the genetic code, e.g. homocysteine, ornithine, D-amino acids, and creatine), natural or artificial mutants or variants or combinations thereof, fusion proteins, derivatized residues (e.g. alkylation of amine groups, acetylations or esterifications of carboxyl groups) and the like are included within the meaning of polypeptide. The peptides that can be used in the present invention consist of multiple amino acids, which may be natural, synthetic or a mixture thereof. Each peptide may express different side chains, if desired. Other amide oligomers such as beta peptides, peptoids and peptide nucleic acids may also be used.

The terms "semiconductor nanocrystal," "SCNC," "quantum dot" and "SCNCTM nanocrystal" are used interchangeably herein and refer to an inorganic crystallite of about 1 nm or more and about 1000 nm or less in diameter or any integer or fraction of an integer therebetween, preferably at least about 2 nm and about 50 nm or less in diameter or any integer or fraction of an integer therebetween, more preferably at least about 2 nm and about 20 nm or less in diameter (for example about 2, 3, 4, 5, 6, 7, 8, 9, 10, 11, 12, 13, 14, 15, 16, 17, 18, 19, or 20 nm). SCNCs are characterized by their uniform nanometer size.

An SCNC is capable of emitting electromagnetic radiation upon excitation (i.e., the SCNC is luminescent) and includes a "core" of one or more first semiconductor materials, and may be surrounded by a "shell" of a second semiconductor material. An SCNC core surrounded by a semiconductor shell is referred to as a "core/shell" SCNC. The surrounding "shell" material will preferably have a bandgap energy that is larger than the bandgap energy of the core material and may be chosen to have an atomic spacing close to that of the "core" substrate.

The core and/or the shell can be a semiconductor material including, but not limited to, those of the groups II-VI (ZnS, ZnSe, ZnTe, US, CdSe, CdTe, HgS, HgSe, HgTe, MgS, MgSe, MgTe, CaS, CaSe, CaTe, SrS, SrSe, SrTe, BaS, BaSe, BaTe, and the like) and III-V (GaN, GaP, GaAs, GaSb, InN, InP, InAs, InSb, and the like) and IV (Ge, Si, and the like) materials, PbSe, and an alloy or a mixture thereof. Preferred shell materials include ZnS.

An SCNC is optionally surrounded by a "coat" of an organic capping agent. The organic capping agent may be any number of materials, but has an affinity for the SCNC surface. In general, the capping agent can be an isolated organic molecule, a polymer (or a monomer for a polymerization reaction), an inorganic complex, or an extended crystalline structure. The coat can be used to convey solubility, e.g., the ability to disperse a coated SCNC homogeneously into a chosen solvent, functionality, binding properties, or the like. In addition, the coat can be used to tailor the optical properties of the SCNC.

Thus, the terms "semiconductor nanocrystal," "SCNC," "quantum dot" and "SCNCTM" as used herein include a coated SCNC core, as well as a core/shell SCNC.

The phrase "one or more sizes of SCNCs" is used synonymously with the phrase "one or more particle size distributions of SCNCs." One of ordinary skill in the art will realize that particular sizes of SCNCs are actually obtained as particle size distributions.

SCNCs for use in the subject methods can be made from any material and by any technique that produces SCNCs having emission characteristics useful in the methods, articles and compositions taught herein. The SCNCs have absorption and emission spectra that depend on their size, size distribution and composition. Suitable methods of production are disclosed in U.S. Pat. Nos. 6,048,616; 5,990,479; 5,690,807; 5,505,928; 5,262,357; PCT Publication No. WO 99/26299; Murray et al. (1993), J. Am. Chem. Soc., 115:8706-8715; and Guzelian et al. (1996), J. Phys. Chem., 100:7212-7219.

Examples of materials from which SCNCs can be formed include group II-VI, III-V and group IV semiconductors such as ZnS, ZnSe, ZnTe, CdS, CdSe, CdTe, MgS, MgSe, MgTe, CaS, CaSe, CaTe, SrS, SrSe, SrTe, BaS, BaSe, BaTe, GaN, GaP, GaAs, GaSb, InAs, InSb, AIS, AlSb, PbS, PbSe, Ge, Si, and ternary and quaternary mixtures thereof.

The composition, size and size distribution of the semiconductor nanocrystal affect its absorption and emission spectra. Exemplary SCNCs that emit energy in the visible range include CdS, CdSe, CdTe, ZnSe, ZnTe, GaP, and GaAs. Exemplary SCNCs that emit energy in the near IR range include InP, InAs, InSb, PbS, and PbSe. Exemplary SCNCs that emit energy in the blue to near-ultraviolet include ZnS and GaN. The size of SCNCs in a given population can be determined by the synthetic scheme used and/or through use of separation schemes, including for example size-selective precipitation and/or centrifugation. The separation schemes can be employed at an intermediate step in the synthetic scheme or after synthesis has been completed. For a given composition, larger SCNCs absorb and emit light at longer wavelengths than smaller SCNCs. SCNCs absorb strongly in the visible and UV and can be excited efficiently at wavelengths shorter than their emission peak. This characteristic allows the use in a mixed population of SCNCs of a single excitation source to excite all the SCNCs if the source has a shorter wavelength than the shortest SCNC emission wavelength within the mixture; it also confers the ability to selectively excite subpopulation(s) of SCNCs within the mixture by judicious choice of excitation wavelength.

The surface of the SCNC is preferably modified to enhance emission efficiency by adding an over-coating layer to form a "shell" around the "core" SCNC, because defects in the surface of the core SCNC can trap electrons or holes and degrade its electrical and optical properties. Addition of an insulating shell layer removes non-radiative relaxation pathways from the excited core, resulting in higher luminescence efficiency. Suitable materials for the shell include semiconductor materials having a higher bandgap energy than the core and preferably also having good conductance and valence band offset. Thus, the conductance band of the shell is desirably of a higher energy and the valence band is desirably of a lower energy than those of the core. For SCNC cores that emit energy in the visible (e.g., CdS, CdSe, CdTe, ZnSe, ZnTe, GaP, GaAs) or near IR (e.g., InP, InAs, InSb, PbS, PbSe), a material that has a bandgap energy in the ultraviolet may be used for the shell, for example ZnS, GaN, and magnesium chalcogenides, e.g., MgS, MgSe, and MgTe. For an SCNC core that emits in the near IR, materials having bandgap energies in the visible range, such as ZnS or CdSe, or the ultraviolet range may be used. Preparation of core-shell SCNCs is described in, e.g., Dabbousi et al. (1997) J. Phys. Chem. B 101:9463; Kuno et al., J. Phys. Chem. 106:9869 (1997); Hines et al., J. Phys. Chem. 100:468; and PCT Publ. No. WO 99/26299. The SCNCs can be made further luminescent through over-coating procedures as described in Danek et al. (1996) Chem. Mat. 8(1):173-180, and Peng et al. (1997) J. Am. Chem. Soc. 119:7019-7029.

Most SCNCs are typically prepared in coordinating solvent, such as TOPO and trioctyl phosphine (TOP), resulting in the formation of a passivating organic layer on the surface of SCNCs with and without a shell. Such passivated SCNCs can be readily solubilized in organic solvents, for example toluene, chloroform and hexane. Molecules in the passivating layer can be displaced or modified to provide an outermost coating that adapts the SCNCs for use in other solvent systems, for example aqueous systems.

The SCNC's, as well as other nanoparticles, may be biofunctionalized for use in, for example, in vivo tissue and cellular labeling, development of biological labels based on quantum dot probes and biosensor development. Other uses of the biofunctionalized materials may include protein ordering for molecular electronics where quantum dots could serve as fluorophores and electronic components, energy harvesting, quantum dot based bar coding, and drug discovery assays where the fluorescence properties of the quantum dots may be combined with bioactive peptides.

The functionalization may be used to impart a variety of properties to quantum dots and/or nanoparticles including, but not limited to, the ability to homogeneously disperse the quantum dots and/or nanoparticles in buffer solutions and a variety of polar solvents at various pH values; biocompatibility; biotargeting by allowing the use of peptide-driven binding to specific cell receptors such as the TAT sequence; providing specific points of modification directly on the quantum dot substrate by using, for example, amine groups for reacting with N-hydroxysuccinimide esters; providing bio-recognized sequences such as the AviTag sequence which is specifically biotinylated as an example; providing protease-recognized cleavage sites; providing polyhistidines for metal affinity coordination; and providing functional groups for further targeted modification, including, for example, amino groups, carboxyl groups, azide groups, alkyne groups, hydrazine groups, aldehyde groups, aminooxy groups, ketone groups, maleimide groups or thiol groups for dye/quencher or other chemical modification steps.

Figure 2:
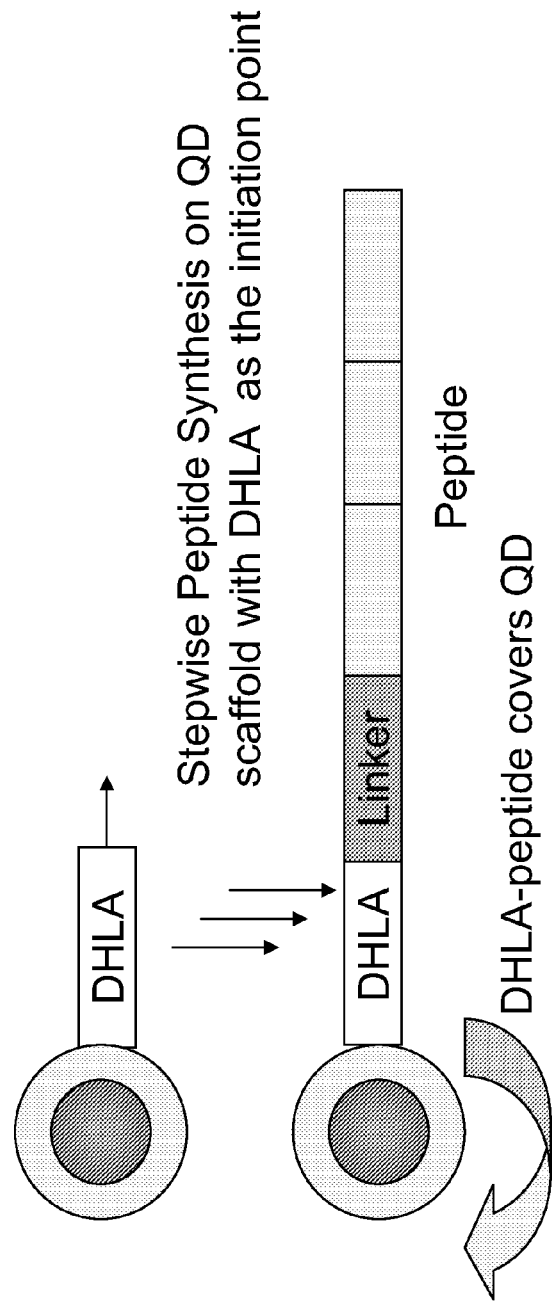
FIG. 2 summarizes three routes for assembling peptides from multiple smaller units which can be employed in the present invention.

In one embodiment of the present invention, peptides are directly synthesized on the quantum dot surface. This may be implemented, for example, (I) by using stepwise solid-state synthesis methods, (II) by stepwise fragment coupling of side chain protected peptides or (III) by stepwise assembly of side chain unprotected peptides using chemical ligation methods as shown in FIG. 2.

FIG. 1 shows a generalized scheme for synthesizing a peptide directly onto a dihydrolipoic acid (DHLA) covered quantum dot surface. The peptide synthesis uses DHLA as the attachment point to the SCNC which is followed by a spacer of variable length (for example polyethylene glycol) and an amino group or carboxylic acid group for starting the peptide synthesis procedure. FIG. 1 shows the assembly of a peptide directly on the SCNC particle. Conjugations can be performed in organic or aqueous solution as desired. Although, in the disclosed version of this method shown in FIG. 1 DHLA is used, other ligands are also applicable such as those having multivalent thiols, monothiols, phosphines or other structures for interaction with the QD surface such as the interactions demonstrated by amphiphilic polymers and dendrimers.

As a result, peptides can be covalently linked directly to the quantum dots in a controlled manner. The peptide(s) to be coupled to the carboxyl group are provided with an amino group for covalent reaction with the carboxyl group.

Coupling agents are typically employed to facilitate or enhance the coupling reaction. Coupling agents may activate the carboxyl groups on the quantum dots. A variety of different coupling agents may be employed including at least DIC/HOBt, EDC/HOBt, BOP, EEDQ, HBTU, PyBOP, HCTU, HATU and DEPBT. The best results were observed with BOP as the coupling agent. The coupling agent activates the acid functionality of the carboxyl group forming a group that can be displaced by the amino group on the peptide to form a covalent bond between the peptide and the quantum dot. This reaction can also be performed in the reverse direction with the amine on the SCNC reacting with an activated carboxylate of the peptide/amino acid.

Activated acid groups that did not react with peptide may be deactivated by adding another compound, such as ethylene diamine. This molecule would react with the activated carboxylate with one of its amine functions. The amine group at the other end provides another positive charge and should therefore increase the water-solubility of the quantum dots. Some cross-linking of the quantum dots could occur, but could be minimized with an excess of ethylene diamine. Alternatively an amino-polyethylene glycol could be utilized to solubilize the QD in a neutral manner without the possibility of cross-linking.

Figure 4:
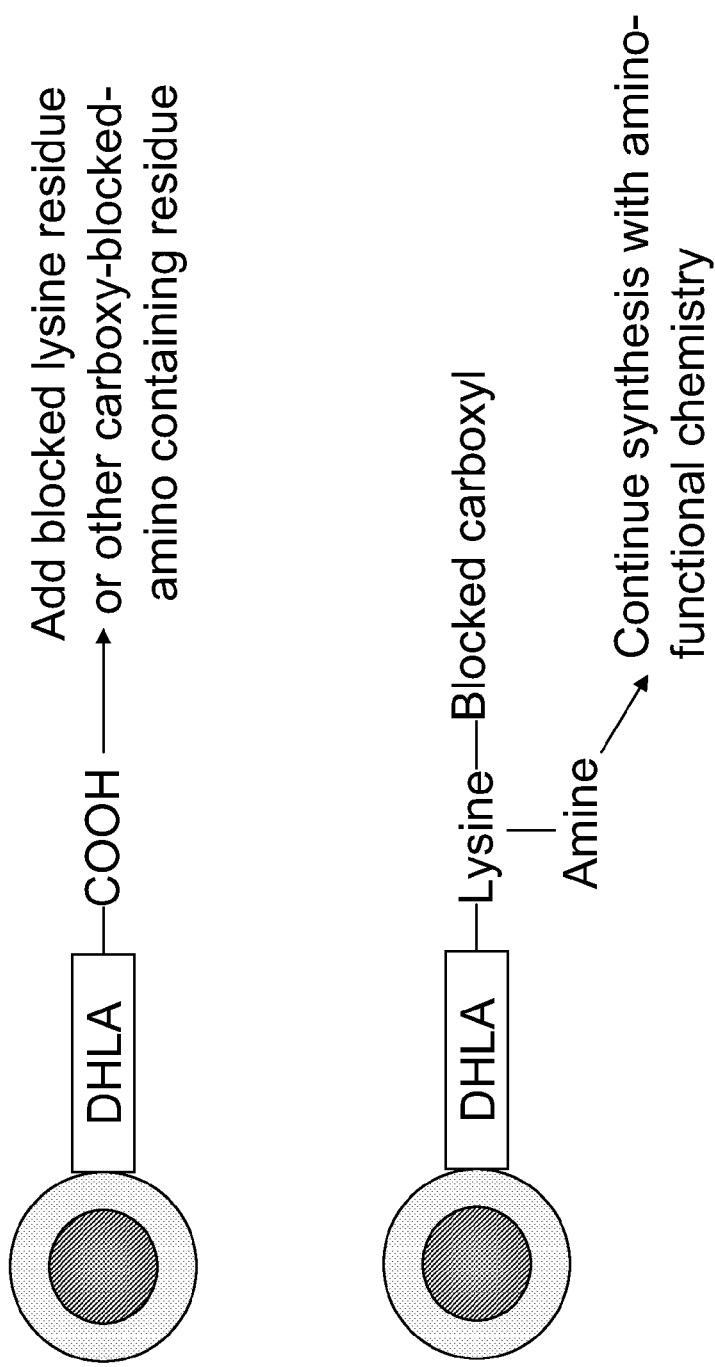
FIG. 4 is a generalized scheme for switching the directionality of peptide synthesis from carboxyl synthesis to amino synthesis by incorporating blocked lysine residues or other amino-containing carboxy-blocked moieties and then utilizing the amine on the residue for further synthesis.

FIG. 4 depicts a generalized scheme for switching the directionality of peptide synthesis from carboxyl synthesis to amino synthesis by incorporating blocked lysine residues. The blocked lysine residues can be used to temporarily or permanently prevent further peptide synthesis by blocking the functional groups which would otherwise react with the peptide. This blocking technique can be used, as shown in FIG. 4, to block the carboxyl group on the quantum dot with an amino-containing residue. The amino-containing residue can then function as a site for further synthesis using the amino group as the reactive group. It is to be understood that carboxyl and amino groups are merely exemplary of the various functional groups which can be used as reactive sites and that other functional groups may be employed within the scope of the present invention. Other suitable functional groups may include, but are not limited to thiols, maleimide/haloacetyl groups, azides, alkyne/hydrazine/aminooxy groups and aldehyde/ketone groups.

Figure 5:
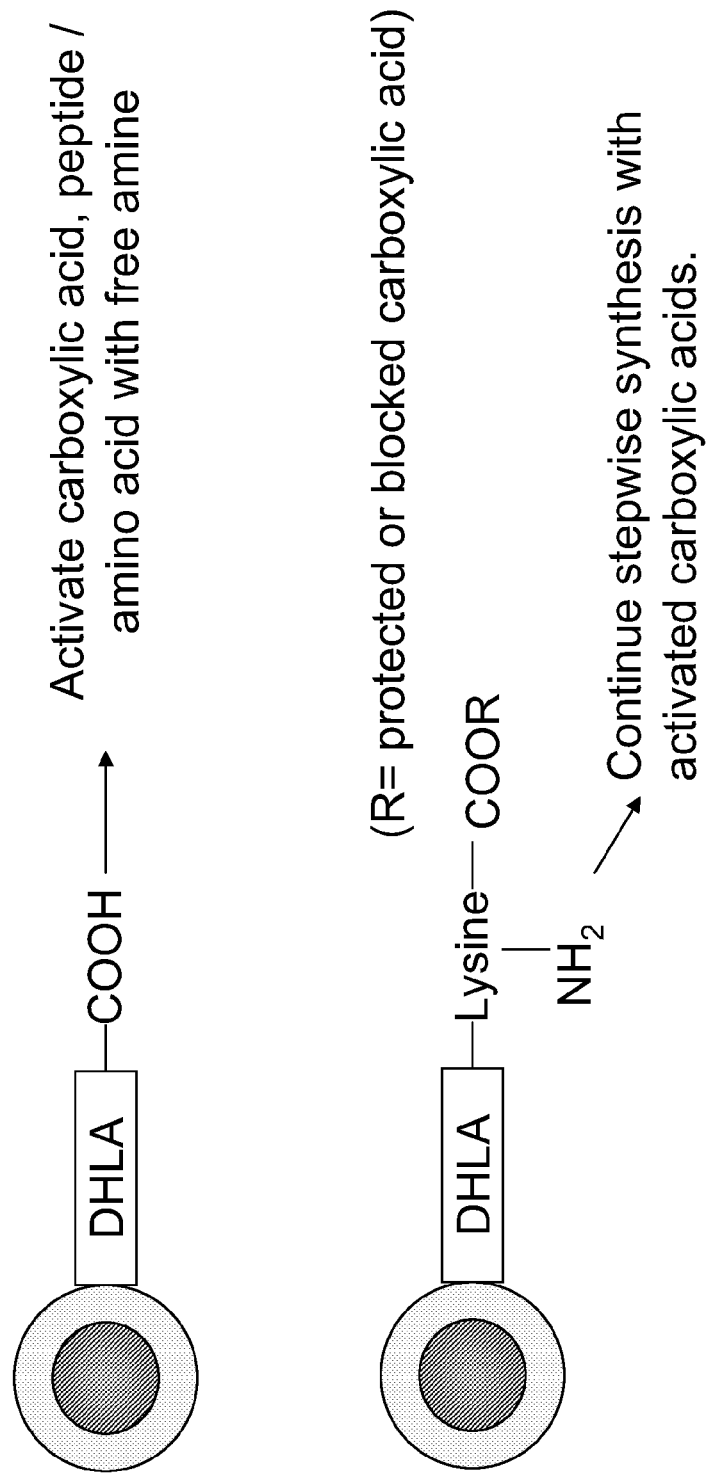
FIG. 5 shows methods of assembling peptides from either carboxyl or amino termini on the quantum dots.

FIG. 5 depicts methods for assembling peptides from either carboxyl or amino termini on the quantum dot. In the case of carboxyl termini, the first step is to activate the carboxylic acid, peptide/amino acid with free amine to provide a reactive amino group. Once an amino group is present, the synthesis is continued with activated carboxylic acids.

Figure 6:
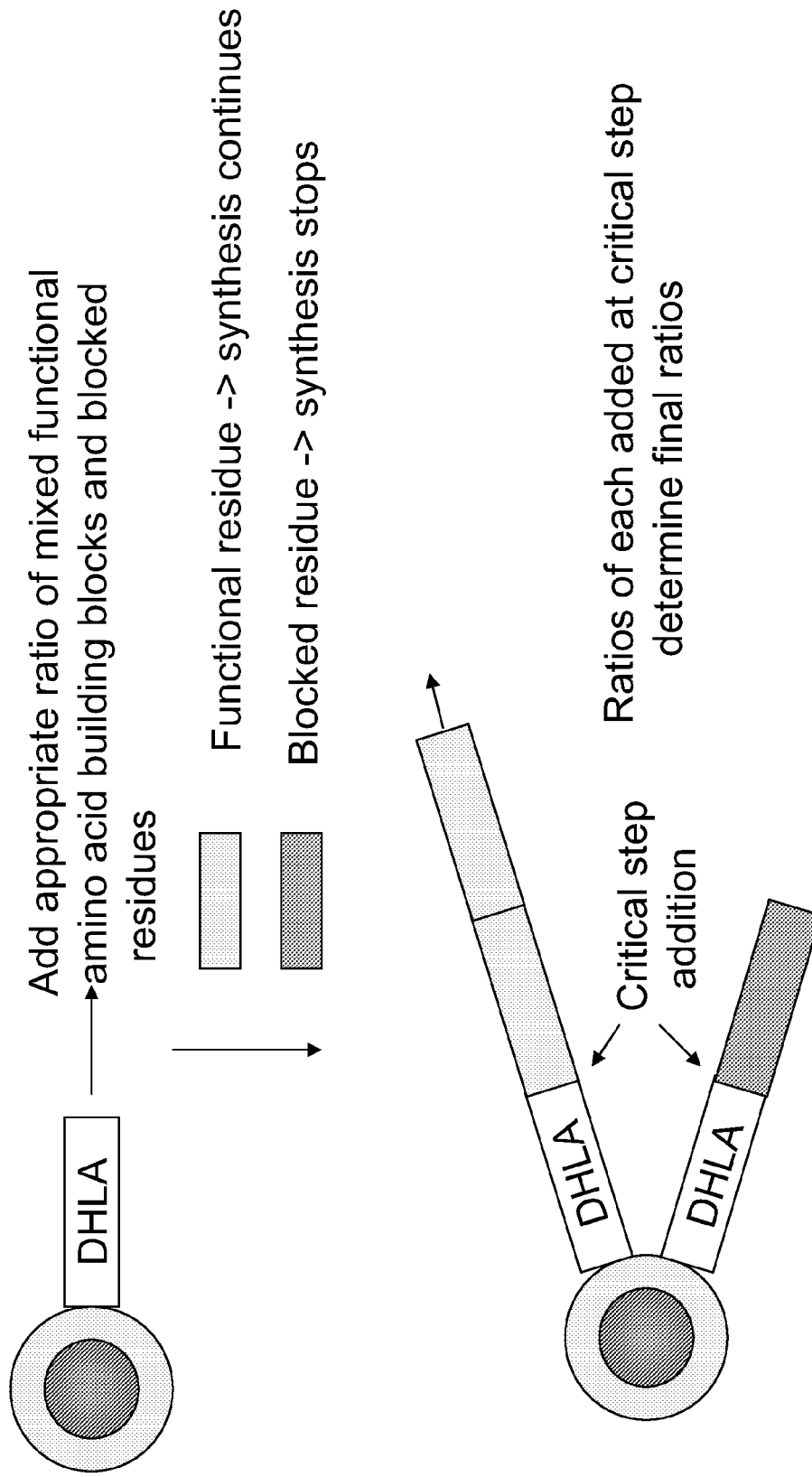
FIG. 6 is a generalized scheme for creating a peptide surface consisting of peptides of different lengths through the addition of blocked and unblocked amino acid building blocks in appropriate ratios.

FIG. 6 depicts a generalized scheme for creating a peptide surface consisting of peptides of different lengths. This is accomplished by partially blocking some of the reactive groups on the surface of the quantum dot in a first step, subsequently reacting the unblocked reactive groups with peptides having one or more additional reactive groups, and then reacting the peptide reactive groups with further peptides which may or may not have one or more additional reactive groups in order to build peptides of different lengths on the quantum dot surface. Also, only a portion of the reactive groups on the peptide already bound to the surface can be reacted with a second peptide and the remaining reactive groups on the first peptide could then be reacted with a third peptide to provide further customization, if desired. These alternatives provide a greater degree of flexibility to the synthesis process by allowing smaller peptides to be used as building blocks to create longer peptides on the surface of the quantum dots.

Figure 7:
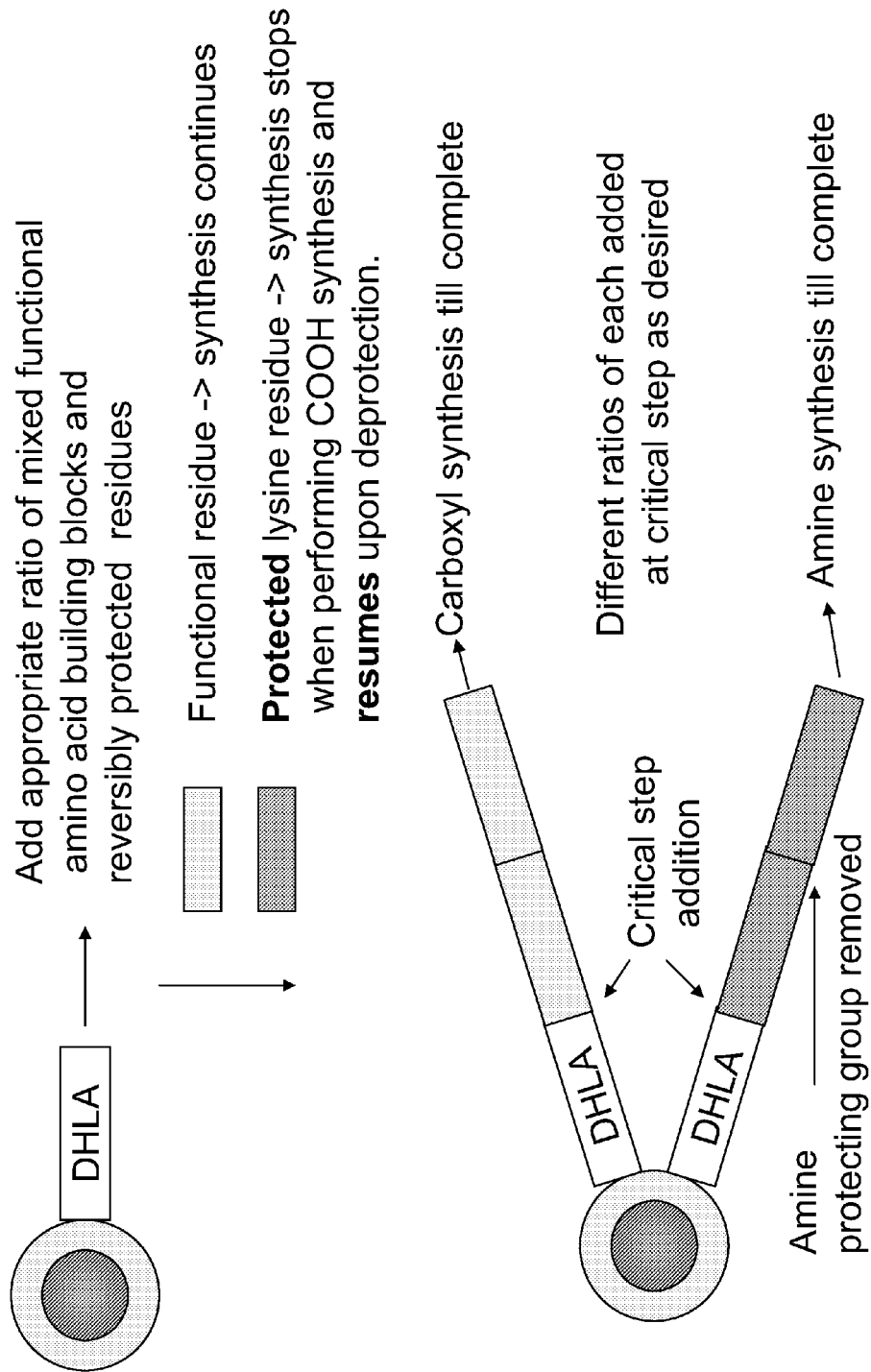
FIG. 7 is a generalized scheme for creating a peptide surface consisting of peptides of different sequences and in different ratios by performing differential synthesis based on concepts shown in FIGS. 3-4. One sequence may be completed while the other is blocked and then another sequence can be added using a different chemical reaction, if desired.

FIG. 7 depicts a scheme for creating a peptide surface consisting of peptides of different lengths based on the concepts shown in FIGS. 3 and 4. The method of FIG. 7 initially follows the methodology of FIG. 6. However, once synthesis of a first set of peptides on the surface of the quantum dot is completed, the blocked reaction sites can be unblocked by any suitable method and further reactions can be carried out at these unblocked sites, for example, for the purpose of providing different peptides on the surface of the quantum dots. It may or may not be necessary to block reactive sites on the already present peptides and thus, depending on the specific chemistry, either approach can be used. It is also possible to attach three or more different peptides directly to the surface of the quantum dots by only partially unblocking the blocked sites in one or more stages, and reacting peptides with the unblocked sites at each stage. Of course the number and/or ratios of the blocked/unblocked sites can be controlled to determine the amount of a particular peptide which will be attached to the surface of the quantum dot in order to allow customization of the properties using this methodology.

Figure 8:
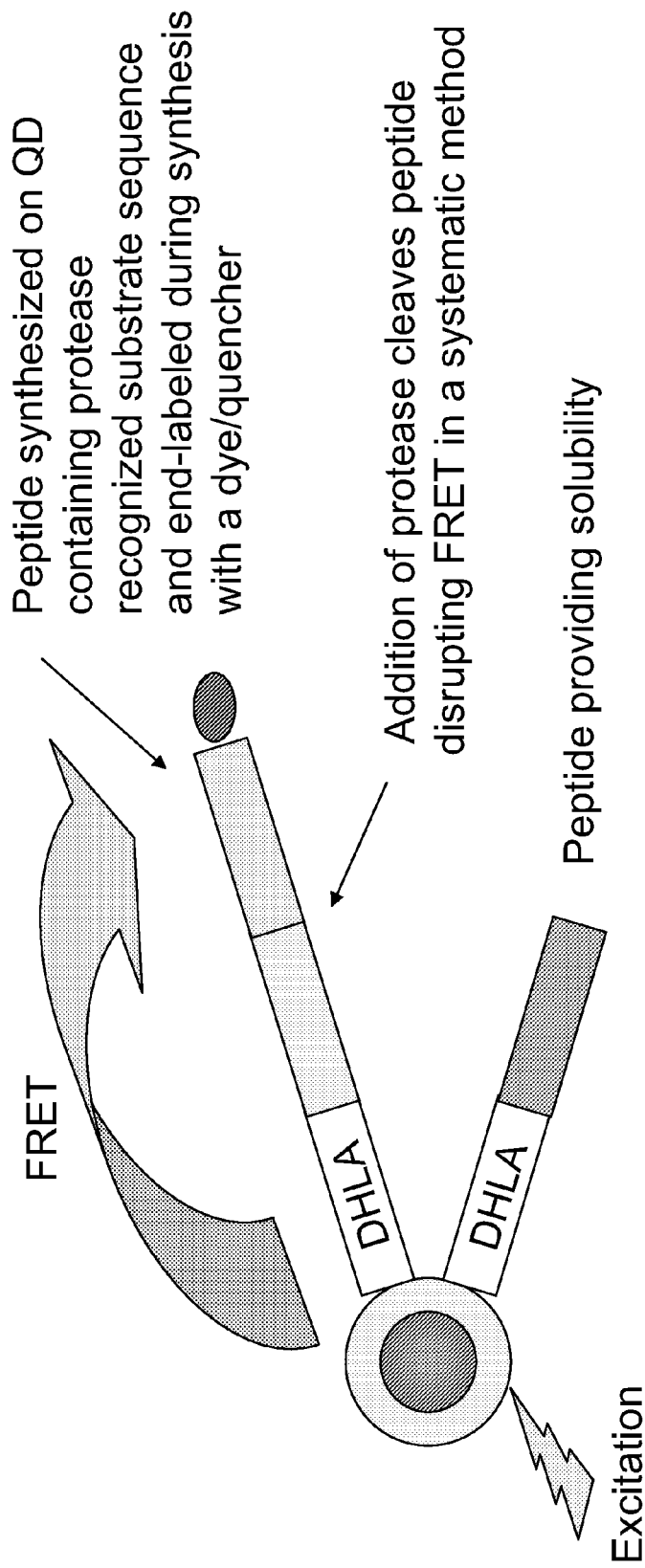
FIG. 8 is a generalized scheme for creating a mixed peptide surface allowing the quantum dot to function as an in vivo/in vitro protease sensor. One peptide imparts solubility to the quantum dot while the other functions in FRET sensing. The size of the peptides may be controlled to prevent potential issues due to steric hindrance.

FIG. 8 shows a generalized scheme for creating a mixed peptide surface allowing the quantum dot to function as an in vivo/in vitro protease sensor. One peptide is attached to the quantum dot to impart solubility to the quantum dot. Another peptide is attached to the quantum dot to provide activity for FRET sensing. The sizes of the peptides are controlled to preclude steric hindrance issues. Thus, this method can be carried out using the general methodology discussed above in relation to FIG. 7.

Figure 9:
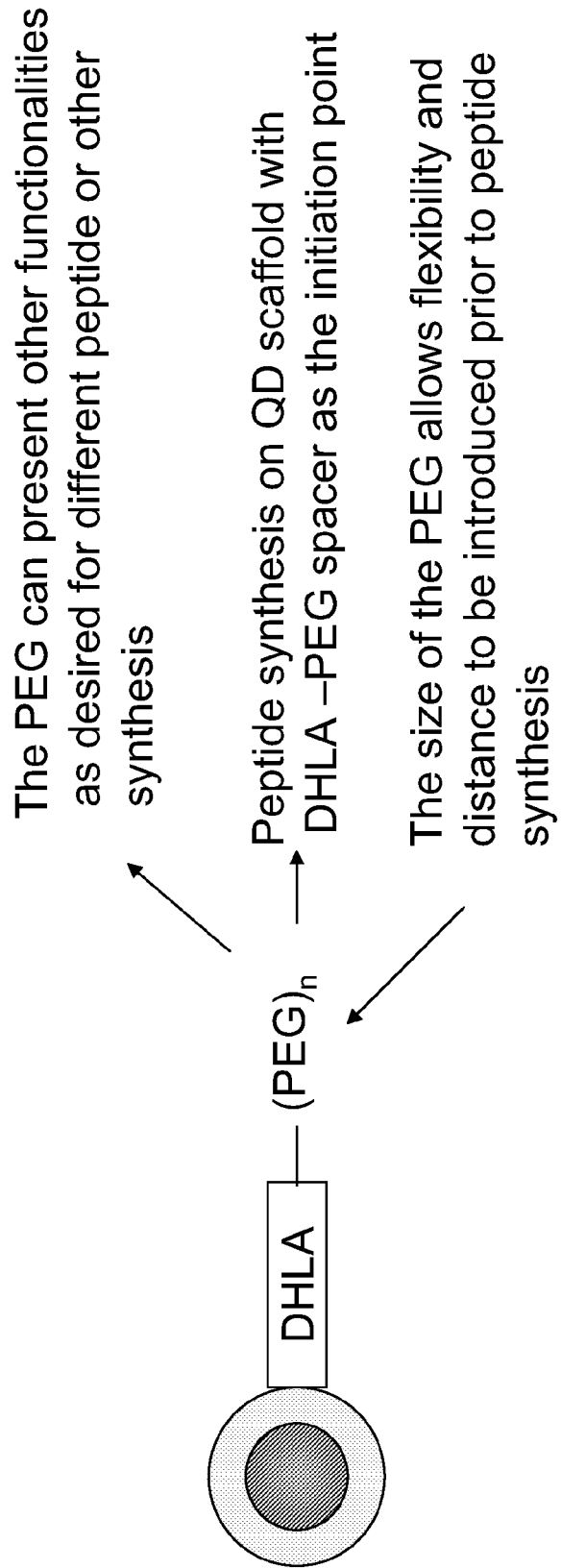
FIG. 9 is a generalized scheme for creating a flexible linker on the quantum dot surface thus allowing the peptide synthesis to begin at a desired distance from the quantum dot surface. This is accomplished by, for example, using DHLA-polyethylene glycol analogs where the analog terminates in a carboxyl or other desired functional group and the size of the polyethylene glycol can be controlled.

FIG. 9 depicts a generalized scheme for creating a flexible linker on the quantum dot surface which allows peptide synthesis to begin at a predetermined, desired distance from the quantum dot surface. This can be accomplished, for example, by using DHLA-polyethylene glycol analogs where the analog terminates in a carboxyl or other desired functional group and the length of the polyethylene glycol moiety can be controlled. In this method, the polyethylene glycol moiety essentially functions as a spacer between the quantum dot and the reactive site (e.g. carboxyl group) to which the peptide will be attached. Other linkers such as hydrocarbons (aminohexanoic acid), short peptides (GlyGlySer and Polyproline), or polysaccharides could be used.

Some quantum dots made by the present invention, for example, those linked to polyarginine, should be able to enter cells and thus biologically active proteins (e.g. antibodies) could be attached to the quantum dots such that specific fluorescence within the cell at targeted sites or binding sites can be achieved.

FIG. 3 provides an outline of some of the functionalities that may be imparted to the quantum dots by peptides and the amino acids they contain, as well as some examples of uses for which these peptides may be employed. In general terms, the present invention may be employed to provide a method to create water soluble and/or biofunctionalized quantum dots and/or nanoparticles. The present methods may, in some embodiments, obviate the need for multiple quantum dot cap exchanges to create biofunctional quantum dots.

Figure 10:
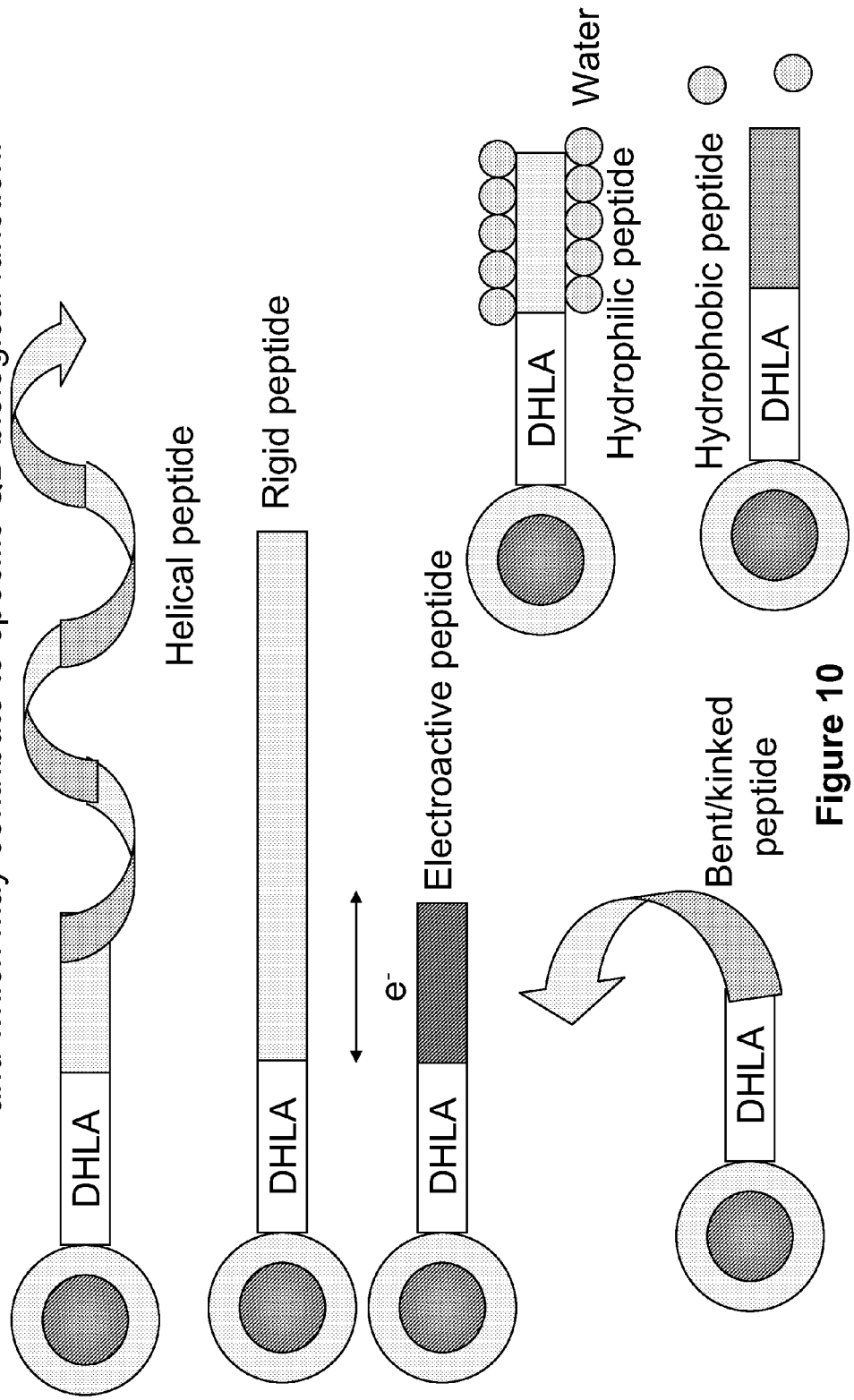
FIG. 10 shows some possible properties of peptides that may be directly synthesized on the quantum dot surface and which may contribute to the final quantum dot biological function.

FIG. 10 depicts some of the possible properties of peptides that can be directly linked to quantum dots using the methodology of the present invention. For example, rigid, flexible, bent or kinked peptides can be employed. Electro-active peptides, hydrophilic peptides and/or hydrophobic peptides can also be employed.

The peptide may contain at least one functionality which imparts a property to said quantum dot or nanoparticle selected from the group consisting of hydrophilicity, hydrophobicity, fluorescence, solubility such as water solubility, electroactivity, cell penetrating ability and binding affinity for an antibody or other biomolecules and biologically active molecules including but not limited to proteins, peptides, DNA, lipids, carbohydrates, and drug or drug-like compounds. Examples of such peptides include "Hairpin peptide beacon: dual-labeled PNA-peptide-hybrids for protein detection." Thurley S, Röglin L, Seitz O. J Am Chem. Soc. 2007 Oct. 24; 129(42):12693-5; "Use of DNA and peptide nucleic acid molecular beacons for detection and quantification of rRNA in solution and in whole cells." Xi C, Balberg M, Boppart S A, Raskin L. Appl Environ Microbiol. 2003 September; 69(9):5673-8.; K. J. Oh, K. J. Cash, A. A Lubin, K. W. Plaxco, Chimeric peptide beacons: A direct polypeptide analog of DNA molecular beacons, Chem. Commun., 46 (2007a) 4869-4871; K. J. Oh, K. J. Cash, V. Hugenberg, K. W. Plaxco, Peptide beacons: A new design for polypeptide-based optical biosensors, Bioconug. Chem., 18 (2007b) 607-609. The peptides may, for example, impart at least two properties to the quantum dot or nanoparticle selected from the group consisting of hydrophilicity, hydrophobicity, fluorescence, solubility, electroactivity, cell penetrating ability and binding affinity for an antibody.

Also, the present invention can be employed to provide a scaffold for peptide synthesis or chemical modification which may optionally be fluorescent thereby allowing, for example, fluorescent monitoring of peptide modification.

In addition, the invention can be used to provide fluorescent quantum dot nanoscaffolds for solid state chemical reactions and/or syntheses and other modifications where the quantum dot can provide both fluorescent and other energy to molecules that surround the surface of the quantum dot to help drive, monitor, and/or control chemical reactions. Alternatively, such quantum dots can be fabricated such that they can be excited by light or energy spectrally distinct from the emitted light wavelengths. The scaffolds can be customized for particular environments to provide resistance to physiochemical degradation.

The present invention provides synthetic schemes for arriving at quantum dots directly functionalized with peptides, for functionalizing quantum dots with different peptides and for synthesizing peptides terminating in a fluorescent dye/quencher directly on the quantum dots providing ready made bio-reagents.

The methods of the present invention are also particularly suitable to provide quantum dots that have multiple different peptides attached directly on the surface whereby quantum dots can be prepared having multiple different functions, including electro-active quantum dots. The quantum dots synthesized by this method can be used, for example, as a central solid-phase support. Also, these methods can be used as a synthetic mechanism for chemically conjugating any small molecule of interest, organic and inorganic, biological and synthetic, to a quantum dot surface using peptide driven chemistry and peptide-derived functionalities as the attachment point(s). The present invention can also be used to control the size of a link between the quantum dot and the point of peptide synthesis.

The methods of the present invention are also advantageous since they may be applied directly to other metallic nanoparticles with all the same utilities and are potentially applicable to a wide variety of metallic surfaces Materials Preparation 1. Quantum Dots CdSe—ZnS core-shell quantum dots were provided from the U.S Naval Research Laboratory in Washington, D.C. They have been prepared as described (Dabbousi et al., "(CdSe)ZnS core-shell quantum dots: Synthesis and characterization of a size series of highly luminescent nanocrystallites," *J. Phys. Chem.*, 101, 9463-9475 (1997) and Mattoussi, H., et al., "Self-assembly of CdSe—ZnS quantum dot bioconjugates using an engineered recombinant protein," *J. Am. Chem. Soc.*, 122, 12142-12140 (2000)), and dihydrolipoic acid (DHLA) has been bound to the surface. It is generally estimated that each quantum dot may feature from approximately two hundred up to 5000 DHLA groups. The quantum dot concentration is 137 μm in DMF. The emission maximum is centered at 510 nm.

2. Synthesis of the Fluorescein Peptide H-GSGFPRGK(Fluorescein)-NH$_2$

All peptides were synthesized using standard protocols as described previously. Synthesis was performed on 0.4 mmol MBHA resin in order to result in a C-terminal amide after HF cleavage. 2.2 mmol of amino acids were used per coupling. After complete chain assembly the Fmoc side chain protection of lysine was removed by a 30 minute treatment with 20% piperidine in DMF 1.2 mmol (3 fold excess) of 5(6)-carboxy fluorescein was dissolved in 2 mL DMF/DCM 1:1 and activated for 15 minutes at 0° C. using 0.6 mmol DIC and 0.72 mmol HOBt. The dye was coupled to the unprotected side chain of lysine for 30 minutes A quantitative ninhydrin test showed complete reaction. After HF cleavage the small peptide was purified by semi-preparative HPLC, lyophilized and stored at −20° C.

3. Synthesis of Poly-Arginine Peptides

H-K(Fmoc)GGRRRRRRR-NH$_2$ (SEQ ID No: 1) was synthesized on a 0.3 mmol scale on MBHA resin using 2.2 mmol amino acids. The Fmoc side chain protection of lysine was not removed in order to increase hydrophobic properties and to allow a quantitative evaluation of bound peptide to the quantum dots. After HF cleavage and lyophilization, the crude Fmoc-peptide was purified and stored at −20° C.

H-K(Fmoc)GGRRRR-NH$_2$ (SEQ ID No: 2) was synthesized with 0.15 mmol MBHA resin using 1.1 mmol of amino acids, 1 mmol HBTU in DMF and 3 mmol DIEA. After HF cleavage, the resulting peptide (C terminal amide) was purified and lyophilized.

4. Coupling of Quantum Dots to the Fluorescein Peptide

Fluorescein-labeled peptide was coupled to 1.37 nmol quantum dots with a maximum of 6.85 μmol carboxyl groups using 1 eq BOP (6.85 μmol) and an excess of base (600 mM). After 10 minutes at room temperature 6.85 μmol peptide in 20 μl DMF was added and the mixture was allowed to react overnight. The solution was then diluted 1:1 with 100 mM HEPES pH 7.5 and washed several times until the flow through was clear. Amicon Microcon microconcentrators (cut-off: 10 kDa) were used at 13000 rpm (100 μl; 8×15 min). In order to increase solubility in HEPES DMSO/HEPES 1:1 was added and diluted 5 times with the buffer. 3 μl of a Trypsin stock (3 mg/L in 100 mM HEPES pH 7.5) was added to digest the peptide within 1 hour. To purify the dots from the cleaved peptide, they were washed several times with 100 mM HEPES pH 7.5. The absorption spectrum was measured from 350 nm to 600 nm.

5. Coupling of Quantum Dots to H-K(Fmoc)GGF:RF:RRRR—NH$_2$

685 μmol of QDs with a maximum of 3.4 mol acid groups were activated with 3.4 μmol EEDQ in 5 μl DMF (100% activation). After 5 minutes activation at room temperature, peptide in 10 μl DMF was added to the mixture and allowed to react for 3 hours. Peptide amounts varied from 0 to 3.4 μmol corresponding to 0, 25, 50, and 75% coverage per dot under the assumption of from about two hundred up to about 5000 acid functions per dot. Unbound peptide and EEDQ were removed by DMF washing steps using Arnicon Ultrafree-MC filters.

6. Quantification of the Coupling

Quantum dot-peptide constructs in DMF were diluted 1:5 with 20% piperidine in DMF for 45 minutes. Quantum dots were separated from the supernatant by filtration with Ultrafree-MC filters. The absorption at 300 nm of the quantum dot-filtrate was measured. Fmoc concentrations were calculated with the Lambert-Beer Law ($\epsilon=7800$ M$^{-1}$ cm$^{-1}$).

7. Controls for Investigation of the Coupling

Two controls were performed. One coupling was done without peptide in order to determine the error of the Fmoc quantification. The experiment was performed in the exact same way as an EEDQ coupling. After piperidine treatment the absorption of the flow through was measured at 300 nm. The other control was done without coupling reagent and using the same amount of peptide as for 25% coupling. This control and the quantum dots from the 25% coupling were mixed with 100 pl of 6 M guanidinium hydrochloride, the solution was separated from the dots (Ultrafree-MC filters) and equal amounts were analyzed with analytical HPLC in order to determine the amount of electrostatically attached peptide.

Example 1

Coupling of the Fluorescein-Labeled Peptide

Figure 11:
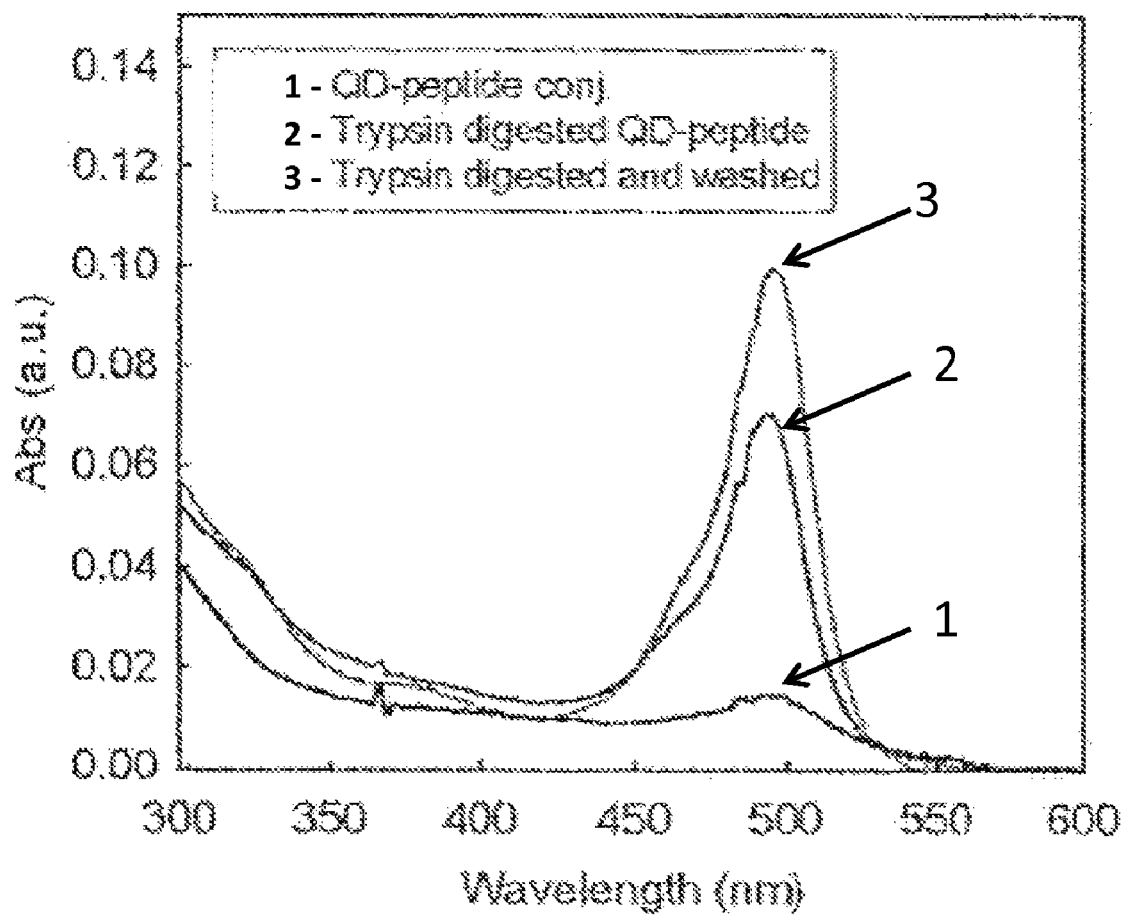
FIG. 11 shows absorption spectra for three solutions of Example 1 showing the dye-labeled peptide coupling to the quantum dot surface, followed by cleavage of the peptide at the arginine site in the presence of trypsin. The large number of dye-labeled peptides on the quantum dot surface dominates the emission and absorption properties of the conjugate solutions, as shown. Cleavage of the arginine site followed by washing away the digested materials results in loss of the dye contribution to the emission and absorption properties and results in recovery of an absorption characteristic of the quantum dots. Picomolar concentrations of the quantum dots have been used for these absorption spectra.

A fluorescein-labeled peptide was coupled to a quantum dot. The peptide H-GSGFPRGK-NH$_2$ was synthesized. 5(6)-carboxy-fluorescein was coupled to the side chain of lysine resulting in a yellow product H-GSGFPRGK(fluorescein)-NH$_2$. This peptide possesses a trypsin cleavage site (H-GS-GFPR"GK(fluorescein)-NH$_2$). Therefore, the fluorescein containing part of the peptide can be cleaved after coupling to the quantum dots. The dots were coupled to the peptide under basic conditions. After washing, the product was very insoluble in aqueous solutions (100 mM HEPES buffer, pH 7.5). This was probably due to the hydrophobic properties of the fluorescein. After trypsin digestion the quantum dots showed an increased solubility. Therefore, measurement of the absorption is only qualitative and not quantitative. Quantum dots absorb as an increasing continuum towards ultraviolet wavelengths at nearly every wavelength short of their first absorption band. Absorption spectra for the materials of this example are given in FIG. 11. A local maximum is observed at 486 nm. The absorbance of the fluorescein-labeled peptide has its maximum at 496 nm due to the labeled dye. When the peptide is bound to the quantum dots, the spectra show the properties of fluorescein but not of the quantum dots. After trypsin digestion and washing the fluorescein peak disappeared and the spectra look similar to the initial QD spectrum.

Example 2

Coupling of a Poly-Arginine Peptide

A peptide sequence H-K(Fmoc)GGRRRRRRR-NH$_2$ (SEQ ID No: 1) having the following features was used for this example:

It is DMF soluble due to the Fmoc group. The coupling reaction has to be performed in organic solvents and the peptide must therefore exhibit high solubility in the solvent (DMF).

The side chain protection of lysine (Fmoc) can be removed using 20% piperidine in DMF. This has two consequences: (a) the peptide becomes more water-soluble as the bulky hydrophobic Fmoc-group is cleaved since the positively charged arginines result in a hydrophilic coat; and (b) the cleaved Fmoc can be used for a quantitative Fmoc determination (absorbance at 300 nm). This allows quantification of the quantum dot-bound peptide.

Poly-arginine peptides are cell penetrating peptides (CPP) (Mitchell, D. J. et al., "Polyarginine enters cells more efficiently than other polycationic homopolymers," *J. Peptide Res.*, 56, 318-325 (2000). This means that if this peptide is bound to the quantum dots, the quantum dots should be able to enter cells. The peptide sequence containing seven arginines was chosen because cells take it up more efficiently than other polycationic homopolymers, although a longer peptide chain (up to 15 arginines) enters cells more efficiently (Mitchell et al., 2000, cited infra). The seven arginine-containing peptide is easier to synthesize and, moreover, it has already been shown that a seven arginine-containing construct facilitates the delivery into the cell (Mitchell et al., 2000, cited infra). The two glycines serve as a spacer between the CPP sequence and the bulky Fmoc on the Lysine side chain.

Several experiments were performed in order to determine the best coupling conditions (coupling with DIC, EDC, or BOP in basic conditions, and EEDQ in a base free environment). The best result was observed with EEDQ as coupling reagent. It needs no base to activate acid groups. This is an advantage as the adding of base was thought to neutralize the acid groups on the quantum dot surface that led to precipitation during the coupling reaction.

The coupled peptide has an Fmoc group on the side chain of lysine. If cleaved with 20% piperidine, it can be used to quantify the amount of bound peptide. The absorption at 300 nm was measured for the different peptide concentrations at 100% activation. Different amounts of peptide were added to the activated acid groups (corresponding to 25, 50, and 75% of the amount of acid groups using the assumption that one quantum dot possesses from about 200 up to an estimated maximum of 5000 carboxylate groups). The Fmoc analysis of the control with no peptide exhibited a putative coupling of 30 peptides per dot. This error comes from inaccurate absorption measurements. In order to determine the contribution of non-covalent binding, a control without any coupling reagent and binding with 25% equivalents of peptide was performed. It resulted in over 80% peptide binding to the quantum dots (233 nmol, 354 peptides per dot). The number of peptides that is attached is comparable to the number of the 25% coupling (244 nmol, 371 peptides per dot).

The results show that increasing amounts of peptide was bound per quantum dot, going as high as nearly 2000 peptides per dot (75% coupling). The plotting of these values indicates that a point of saturation has not been reached and the limit of the amount that can be coupled to quantum dots could not be determined. 100% coupling was not performed and therefore it is not appropriate to formulate a regression. However, the number of peptides per dot seems to be strongly correlated to the amount of added peptide. The percentage of maximal coupling is considerably smaller than the observed coupling. It could be possible that EEDQ did not activate all acid groups. Although one equivalent of coupling reagent was added it is likely that some acid groups did not react with EEDQ. A second reason is that the amount of acid groups is undetermined. The number lies between 1000 and 5000. Kinetics seems to play a role in the covalent binding as higher concentrations lead to higher peptide coverage than would be expected if the covering was linear.

6M guanidine hydrochloride having pH 4 was added to the quantum dots and reacted overnight. This denaturing reagent is used to elute all non-covalent bound peptide. After separation from the quantum dots, an analytical HPLC of the flow through (injection of equal amounts) demonstrated that 4.5 times more peptide came off the control than off the EEDQ activated quantum dots. This leads to the conclusion that approximately 22% of the peptides are attached to the surface through electrostatic forces. This conclusion was confirmed as no peptide came off in a second control.

The resulting dots were soluble in aqueous solutions due to the hydrophilic coat of polyarginine peptides.

It has been shown that it is possible to conjugate peptides covalently to quantum dots. In general, the developed technique should be applicable for every peptide or protein that is soluble in DMF. The quantum dot-peptide constructs show water solubility due to the introduction of a hydrophilic coat and can therefore be applied for biomedical research. The quantum dots linked to polyarginine should be able to enter cells and thus biologically active proteins (e.g. antibodies) could be attached to the dots that would lead to specific targeted fluorescence labeling within the cell.

The amount of peptide/protein that can be coupled to one dot varies. This is possibly due to the size as bigger molecules introduce increased steric hindrance. Therefore, it is important to be able to quantify the efficiency of the coupling reaction. By coupling the poly-arginine peptide, water-soluble biocompatible quantum dots are obtained. This important feature is the basic key for many biological applications.

The foregoing examples have been presented for the purpose of illustration and description only and are not to be construed as limiting the scope of the invention in any way. The scope of the invention is to be determined from the claims appended hereto.

mers, and dendrimers which interact with the quantum dot or nanoparticle surface; or (B) the quantum dot or nanoparticle reactive functional groups comprise carboxyl groups and the peptide reactive functional groups comprise amino groups.

2. A method as claimed in claim 1, wherein the material used to functionalize the surface of the quantum dot or nanoparticle is said DHLA.

What is claimed as new and desired to be protected by Letters Patent of the United States is:

1. A method for covalent attachment of peptides to quantum dots or nanoparticles comprising the steps of:
   functionalizing at least a portion of a surface of the quantum dot or nanoparticle with one or more materials having at least one reactive functional group therein; and
   reacting a peptide having a reactive functional group with at least some of the quantum dot or nanoparticle reactive functional groups to covalently bond at least some of the peptide to the quantum dots or nanoparticles so that peptides are directly synthesized on the quantum dot or nanoparticle surface by (I) stepwise solid-state synthesis methods, (II) stepwise fragment coupling of side chain protected peptides or (III) stepwise assembly of side chain unprotected peptides using chemical ligation methods,
   wherein
   (A) the material used to functionalize the surface of the quantum dot or nanoparticle is selected from the group consisting of DHLA, DHLA-polyethylene glycol analogs, ligands including at least one of mono- and multivalent thiols, phosphines, amphiphilic poly- 3. A method as claimed in claim 1, wherein the peptide comprises at least two reactive functional groups and further comprising the step of:
   reacting a second peptide having a reactive functional group with at least some of the reactive functional groups of the peptide already bound to the quantum dot or nanoparticle to covalently bond at least some of the second peptide to the peptide already bound to the quantum dot or nanoparticle.

4. A method as claimed in claim 3, wherein only a portion of the reactive groups on the peptide attached to the quantum dot or nanoparticle is reacted with the second peptide and further comprising the step of:
   reacting a third peptide having a reactive functional group with at least some of the reactive functional groups of the peptide already bound to the quantum dot or nanoparticle to covalently bond at least some of the third peptide to the peptide already bound to the quantum dot or nanoparticle.

5. A method as claimed in claim 1, further comprising the step of:
   blocking a portion of the reactive functional groups attached to the surface of the quantum dot or nanoparticle prior to the step of reacting the reactive functional group of the peptide with said reactive functional groups attached the surface of the quantum dot or nanoparticle, and wherein the reactive functional group of the peptide is subsequently reacted with at least some of the reactive functional groups attached the surface of the quantum dot or nanoparticle that remain unblocked after the blocking step.

6. A method as claimed in claim 5, further comprising the steps of:
unblocking at least some of the blocked reactive functional groups attached to the surface of the quantum dot or nanoparticle after the step of reacting the peptide with at least some of the unblocked reactive functional groups; and
subsequently reacting a second peptide having a reactive functional group with at least some of the reactive functional groups attached to the surface of the quantum dot or nanoparticle which were unblocked in said unblocking step to covalently attach said second peptide to the surface of the quantum dot or nanoparticle.

7. A method as claimed in claim 5, further comprising the steps of:
reacting a second peptide having a reactive functional group with at least some of the reactive functional groups of the peptide already bound to the quantum dot or nanoparticle to covalently bond at least some of the second peptide to the peptide already bound to the quantum dot or nanoparticle;
unblocking at least some of the blocked reactive functional groups attached to the surface of the quantum dot or nanoparticle after the step of reacting the peptide with at least some of the unblocked reactive functional groups; and
subsequently reacting a third peptide having a reactive functional group with at least some of the reactive functional groups attached to the surface of the quantum dot or nanoparticle which were unblocked in said unblocking step to covalently attach said third peptide to the surface of the quantum dot or nanoparticle.

8. The method of claim 7, wherein the second and third peptides are the same.

9. The method of claim 7, wherein the second and third peptides are different.

10. The method of claim 1, wherein the peptide contains at least one functionality which imparts a property to said quantum dot or nanoparticle selected from the group consisting of hydrophilicity, hydrophobicity, fluorescence, solubility, electroactivity, cell penetrating ability, and binding affinity for one of an antibody, proteins, peptides, peptide nucleic acid hybrids, DNA, lipids, carbohydrates and drug or drug-like compounds.

11. The method of claim 3, wherein the peptides impart at least two properties to the quantum dot or nanoparticle selected from the group consisting of hydrophilicity, hydrophobicity, fluorescence, solubility, electroactivity, cell penetrating ability and binding affinity for an antibody.

12. The method of claim 11, wherein said property is water solubility.

13. The method of claim 11, wherein said property is binding affinity for a specific antibody.

14. The method of claim 11, wherein said property is fluorescence.

15. The method of claim 6, wherein the peptides impart at least two properties to the quantum dot or nanoparticle selected from the group consisting of hydrophilicity, hydrophobicity, fluorescence, solubility, electroactivity, cell penetrating ability and binding affinity for an antibody.

16. The method of claim 1, further comprising the step of:
reacting a linker molecule having at least two reactive functional groups with at least some of the quantum dot or nanoparticle reactive functional groups to covalently bond at least some of the linker to the quantum dots or nanoparticles prior to the peptide reacting step, and wherein the peptide reactive functional group reacts with a functional group of the linker molecule in the peptide reacting step.

* * * * *